United States Patent [19]

Grasso

[11] 4,359,580

[45] Nov. 16, 1982

[54] PROCESS FOR THE PREPARATION OF SULFUR YLIDE INTERMEDIATES OF INSECTICIDAL PYRETHROIDS

[75] Inventor: Charles P. Grasso, East Windsor, N.J.

[73] Assignee: American Cyanamid Company

[21] Appl. No.: 233,750

[22] Filed: Feb. 12, 1981

Related U.S. Application Data

[63] Continuation of Ser. No. 65,391, Aug. 9, 1979, abandoned.

[51] Int. Cl.³ ............................................. C07D 333/46
[52] U.S. Cl. ............................................ 549/79; 560/8
[58] Field of Search ........................................... 549/79

[56] References Cited

U.S. PATENT DOCUMENTS 4,083,863 4/1978 Brand ..................................... 549/79

OTHER PUBLICATIONS

Payne, George B. *J. Org. Chemistry*, vol. 32, pp. 3351–3355 (1970).

Lowe, P. A. *Chemistry and Industry*, pp. 1070 and 1076 (1970).

*Primary Examiner*—Natalie Trousof
*Assistant Examiner*—L. Hendriksen
*Attorney, Agent, or Firm*—H. G. Jackson

[57] ABSTRACT

The invention is an improved process for the preparation of lower alkyl esters of tetrahydrothiophenium carboxymethylide intermediates of insecticidal pyrethroids, and to insecticidal prethroids derived from said ylides.

1 Claim, No Drawings

PROCESS FOR THE PREPARATION OF SULFUR YLIDE INTERMEDIATES OF INSECTICIDAL PYRETHROIDS

This is a continuation of application Ser. No. 65,391, filed Aug, 9, 1979, now abandoned.

The present invention relates to an improved process for the preparation of lower alkyl esters of tetrahydrothiophenium carboxymethylide of formula (I):

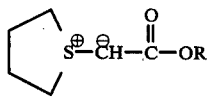

wherein R is $C_1$–$C_4$ alkyl, by a heterogeneous phase reaction comprising reacting a lower alkyl ester of a 1-(carboxymethyl)tetrahydrothiophenium halide salt of formula (II):

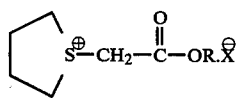

wherein R is as defined above and X is bromine or chlorine; with an anhydrous alkali metal hydroxide such as sodium or potassium hydroxide in the presence of an inert water immiscible solvent. On completion of the reaction, the insolubles present in the reaction mixture are mechanically separated from the solution of the formula (I) ylide. This solution may be used directly in subsequent reaction, or the yield may be isolated therefrom, if so desired.

The hereinabove briefly described process of the present invention has certain advantages when compared to known methods of the art utilized for the preparation of ylides, such as the process disclosed and claimed by W. W. Brand in U.S. Pat. No. 4,083,863 (issued Apr. 11, 1978) for the preparation of analogous tetrahydrothiophenium ylides and the pyrethroids prepared therefrom.

Notably, the by-products of the present process are solids, easily removable from the reaction mixture by mechanical means. Thus the problem of disposal of large amounts of highly alkaline effluents into the environment, and therefore contamination of same is avoided. Although at the present time effluents of the type described above and generated by the Brand process may be barged to sea and disposed there by dumping, this practice will be prohibited in the near future.

We also find that since the by-product of the present process is separated from the reaction as a solid mixture, wherein the components of the mixture comprise primarily alkali metal halide(s) and hydroxide(s), these may be easily and economically recovered from said mixture, if so desired.

Thus an "ylide" of formula (I) may be prepared by the process of the present invention as illustrated and described below:

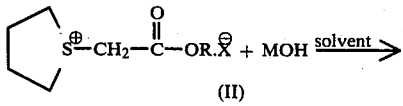

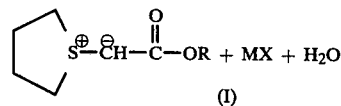

wherein R is $C_1$–$C_4$ alkyl, preferably ethyl; X is bromine or chlorine; M is sodium or potassium, preferably sodium.

Accordingly, a lower alkyl ester of a 1-(carboxymethyl)tetrahydrothiophenium halide of formula (II) is reacted with a solid, particulate alkali metal hydroxide of sodium or potassium hydroxide, preferably sodium hydroxide in a molar ratio of from about 1:1 to about 1:3 and preferably 1:2 to 1:3 in the presence of an inert water immiscible solvent of methylene chloride, chloroform, ethylene dichloride or mixtures thereof, in the temperature range of from about 0° C. to about 35° C. and preferably 20° to 30° C. for a period of time of from about one to five hours or until the reaction is essentially complete. The above heterogeneous phase reaction may be run under a blanket of inert dry gas such as nitrogen, if so desired, to prevent atmospheric moisture from entering the reaction vessel. The alkali metal hydroxide may be in the form of flakes, powder, pels or some other suitable particulate shape, although "pels" are preferred. On completion of the reaction, the mixture is filtered and the solution of the thus prepared ylide (I) may be used "as is" in the subsequent step leading to insecticidal pyrethroids, or said ylide may be isolated from the above solution if so desired.

It is recognized, that the use of excess anhydrous base also acts as a drying agent for the reaction system, hence there is less need to be concerned about the presence of small amounts of water in said reaction system, as is shown in Table I of Example 3.

Thus a cyclopropanecarboxylate of formula (IV), a key intermediate in the preparation of insecticidal pyrethroids, may be made from the ylide (I) as follows:

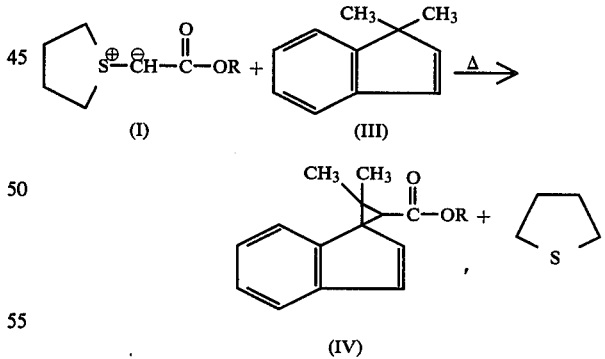

wherein R is as hereinabove defined.

In practice, about 0.9 to 1.0 molar equivalent of dimethylbenzofulvene (III) is added to the solution of the above ylide (I), the solvent is removed under vacuum at about 50° C. to 60° C., and the residue heated under vacuum at 50°–60° C. for a period of about 6 to 24 hours and preferably 6 to 8 hours until the reaction is essentially complete. The tetrahydrothiophene is recovered by distillation at 90° C. under vacuum, while the desired cyclopropanecarboxylate (IV) is recoverable from the reaction vessel.

The advantages and versatility of tetrahydrothiophenium ylides (I) in the preparation of cyclopropanecarboxylic acids, esters, and the insecticidal pyrethroids derived therefrom are well documented and illustrated in U.S. Pat. No. 4,083,863 (issued Apr. 11, 1978 to W. W. Brand; Assignee: American Cyanamid Company), and the information contained therein is incorporated in the present application by way of reference.

The present invention is further illustrated by the following non-limiting examples.

EXAMPLE 1

Preparation of Tetrahydrothiophenium, Carboxymethylide, Ethyl Ester

Powdered potassium hydroxide (0.65 g; 0.01 mol) is added at room temperature to a vigorously stirred mixture of ethyl 1-(carboxymethyl)tetrahydrothiophenium bromide (2.5 g; 0.01 mol) and methylene chloride (20 ml). Stirring is continued for 15 minutes, the organic layer is then decanted and filtered. The solid residue from the reaction mixture is washed with methylene chloride (2×10 ml), the washings are decanted, filtered and combined with the above solution. The organic solution is concentrated at 40° C. under vacuum, and the residue held under vacuum at room temperature for ½ hour to afford 1.66 g (95%) of title product, a clear oil.

EXAMPLE 2

Preparation of the Ethyl Ester of 3,3-dimethylspiro[cyclopropane-1,1'-indene]-2-carboxylic acid Sodium hydroxide pels (44.0 g; 1.1 mol) are added to a stirred slurry of ethyl 1-(carboxymethyl)tetrahydrothiophenium bromide (187.0 g of 75% real; 0.55 mol) in methylene chloride (500 ml) at 18°–20° C. The reaction mixture is stirred vigorously for 2 hours, is then filtered and the isolated solids washed with methylene chloride (2×100 ml). The filtered solution and washings are combined and added to dimethylbenzofulvene (91.0 g of 85.7% pure; 0.5 mol). The mixture is heated at 50° C. and the solvent removed under vacuum in about 1.25 hours. The reaction mixture is then held under vacuum at 55° C. for 22 hours and at room temperature for 36 hours. Analysis of a sample indicates the reaction mixture to contain 93% by weight of title product and 4.8% by weight of dimethylbenzofulvene. The latter is removed from the reaction mixture by heating same at 80° C. under vacuum for 1.5 hours.

EXAMPLE 3

Evaluation of the effect of moisture, reaction time and the molar ratio of base to "sulfonium salt" on the formation of the corresponding "sulfonium ylide"

By the method of Example 2 a number of experiments are run in which the amount of sodium hydroxide pels is varied between 1.1 and 3 moles per mole of ethyl 1-(carboxymethyl)tetrahydrothiophenium bromide. The reaction time is varied between 1.5 and 5 hours, while the methylene chloride used as reaction solvent is either anhydrous ("dry") or is saturated with water (at the temperature range the reaction is run).

The thus-formed ylide is then reacted with dimethylbenzofulvene at 55° C. for a period of 18 hours by the procedure of Example 2, to afford the ethyl ester of 3,3-dimethylspiro[cyclopropane-1,1'-indene]-2-carboxylic acid. On completion of the reaction, the amount of product obtained is determined by gas chromatography (G.C.).

Pertinent data, including the results of G.C. analyses are compiled in Table I below, wherein it can be clearly seen that increased base concentrations have a major positive effect, the presence of water has a significant negative effect on the yields obtainable, while an almost equal positive interaction is noted between excess base and moisture content.

TABLE I

Reaction scheme:

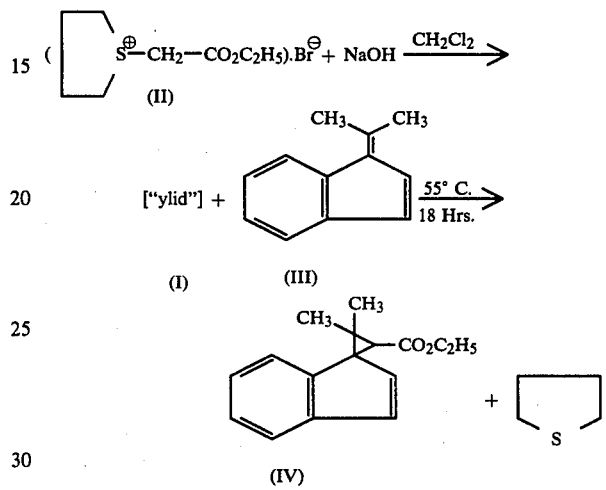

| | | CH$_2$Cl$_2$ | | | |
|---|---|---|---|---|---|
| Experiment | Molar Ratio NaOH:(II) | Dry | Saturated with H$_2$O | Reaction time hours | Percent Yield of (IV) | Percent Recovery of (III) |
| 1 | 1.1:1 | + | | 3 | 60.9 | 36.2 |
| 2 | 1.1:1 | | + | 3 | 45.9 | 49.0 |
| 3 | 1.1:1 | + | | 1.5 | 70.6 | 27.3 |
| 4 | 1.1:1 | | + | 1.5 | 44.2 | 46.3 |
| 5 | 2:1 | + | | 3 | 87.7 | 10.4 |
| 6 | 2:1 | | + | 3 | 85.8 | 12.5 |
| 7 | 2:1 | + | | 1.5 | 85.3 | 13.7 |
| 8 | 2:1 | | + | 1.5 | 86.6 | 12.0 |
| 9 | 2:1 | * | | 5 | 87.0 | 11.8 |
| 10 | 3:1 | * | | 2 | 90.6 | 8.6 |

*Standard reagent grade, not dried.

We claim:
1. A method for the preparation of a compound of the formula

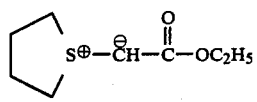

which comprises reacting a compound of the formula

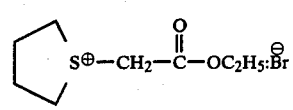

with solid particulated sodium hydroxide used in 2:1 to 3:1 molar amount per mole of the compound of formula II in a solvent of methylene chloride, and a temperature range of 20° C. to 30° C.

* * * * *